(12) United States Patent
Arnold

(10) Patent No.: US 8,202,908 B1
(45) Date of Patent: Jun. 19, 2012

(54) D-ASPARTIC ACID SUPPLEMENT

(75) Inventor: Patrick Arnold, Champaign, IL (US)

(73) Assignee: Thermolife International, LLC, Phoenix, AZ (US)

( * ) Notice: Subject to any disclaimer, the term of this patent is extended or adjusted under 35 U.S.C. 154(b) by 349 days.

(21) Appl. No.: 12/383,682

(22) Filed: Mar. 27, 2009

Related U.S. Application Data

(60) Provisional application No. 61/072,254, filed on Mar. 28, 2008.

(51) Int. Cl.
*A61K 31/195* (2006.01)
*A61K 9/24* (2006.01)
*A61P 15/08* (2006.01)

(52) U.S. Cl. .................. 514/561; 424/464

(58) Field of Classification Search ............. 514/561; 424/464
See application file for complete search history.

(56) References Cited

U.S. PATENT DOCUMENTS 5,397,786 A * 3/1995 Simone .............. 514/300
5,691,377 A * 11/1997 Estienne et al. ........... 514/557

* cited by examiner

*Primary Examiner* — Sreeni Padmanabhan
*Assistant Examiner* — Uma Ramachandran
(74) *Attorney, Agent, or Firm* — Booth Udall, PLC

(57) ABSTRACT

The physical condition of adult male humans of all ages is improved by administering an effective amount of a D-aspartic acid compound. The administration of this compound increases their levels of testosterone, growth hormone, and/or insulin-like growth factor.

2 Claims, No Drawings

D-ASPARTIC ACID SUPPLEMENT

CROSS-REFERENCE TO RELATED APPLICATION

This application claims the benefit of U.S. Provisional Application Ser. No. 61/072,254, Mar. 28, 2008.

FIELD OF THE INVENTION

This invention relates to nutritional supplements for male humans.

BACKGROUND OF THE INVENTION

1. Aspartic Acid

Aspartic acid is an amino acid having the formula HOOC—$CH_2$—CH($NH_2$)—COOH. Its conjugate base (formed by losing a proton) is known as aspartate. For example, sodium aspartate NaOOC—$CH_2$—CH($NH_2$)—COOH is the sodium salt of aspartic acid. Aspartic acid and aspartate are biologically equivalent in most respects and the term "aspartic acid" is used herein to refer to both compounds.

Closely related derivatives of aspartic acid are also known. One class of derivatives, known as esters, are formed by substituting an —OR' group (where R' represents an alkyl or an aryl group) for the —OH in one of the carboxylic groups (—COOH). For example, methyl aspartate $CH_3$OOC—$CH_2$—CH($NH_2$)—COOH is an ester. Another type of derivative is formed by substituting a methyl group (—$CH_3$) for one of the hydrogens of the amino group (—$NH_2$). For example, N-methyl-aspartate is a derivative having the formula HOOC—$CH_2$—CH(NH$CH_3$)—COOH. Aspartic acid, its salts such as sodium aspartate, its esters such as methyl aspartate, and other derivatives such as N-methyl-aspartate are nearly biologically equivalent in some respects and the term "aspartic acid compound" is used herein to refer to them.

In aspartic acid, the carbon atom attached to the amino group is asymmetric, i.e., it has four different groups attached to it. The presence of an asymmetric carbon makes aspartic acid a member of the class of compounds that exists in one of two optically active forms. The two forms, known as enantiomers, are mirror images of each other. They differ only in the orientation of the four groups that are attached to the asymmetric carbon.

Enantiomers have identical chemical properties except toward optically active reagents. Optically active reagents are very common in biological systems. As a result, enantiomers often have very different functions in the body.

Enantiomers are sometimes analogized to a right hand and a left hand. The two hands are mirror images of each other and are identical in most respects. However, they differ dramatically in how they fit within a right-handed glove.

One of the two enantiomers of aspartic acid is known as levorotatory aspartic acid or by the abbreviations (−)-aspartic acid, (l)-aspartic acid, or L-aspartic acid. The other enantiomer of aspartic acid is known as dextrorotary aspartic acid or by the abbreviations (+)-aspartic acid, (d)-aspartic acid, or D-aspartic acid. A mixture of equal parts of both enantiomers is known as a racemic mixture, a racemic modification, or a racemate and is designated as (±)-aspartic acid or DL-aspartic acid. The terms L-aspartic acid and D-aspartic acid are used herein for the enantiomers and DL-aspartic acid is used for the racemic mixture.

L-aspartic acid is one of the twenty-six amino acids that make up proteins. L-aspartic acid is a common nutritional supplement.

D-aspartic acid is also present in the human body, but in much smaller amounts than L-aspartic acid. As discussed in the following sections, D-aspartic acid is believed to play a role in the generation of certain hormones in male humans.

2. Male Hormones

Hormones are molecules that carry signals from one group of cells to another group of cells. Three such hormones are testosterone, growth hormone (GH), and insulin-like growth factor 1 (IGF-1).

Testosterone is the major male sex hormone in humans and other mammals. It is produced primarily in the testes. Testosterone is responsible for a wide range of beneficial effects, including increases in muscle mass, strength, and sexual performance. Growth hormone is produced in the pituitary gland and is also responsible for a wide range of beneficial effects, including increases in muscle mass. Insulin-like growth hormone 1 is produced in the liver and is further responsible for a wide range of beneficial effects.

These three hormones are at their highest levels during young adulthood when physical condition (including athletic and sexual performance) is greatest. The levels typically decline gradually as men age. Many of the undesirable effects of aging are believed to be caused by the declining levels of hormones. It is believed that increasing the levels of these three hormones improves the physical condition of adult males of all ages. However, increasing the levels by simply adding the hormones carries with it certain disadvantages.

3. The Production Of Male Hormones

The production of testosterone, growth hormone (GH), and insulin-like growth factor 1 (IGF-1) hormones in male mammals is regulated by a complex and not fully understood communication system between the hypothalamus gland located at the base of the brain, the pituitary gland (another gland located at the base of the brain), the liver, and the testes.

In the case of testosterone, its production is believed to be at least partially controlled by the following system and pathways in male humans. The hypothalamus has receptors that detect the level of testosterone in the blood. When the level becomes low, the hypothalamus generates a gonadotropin releasing hormone (GnRH) that is detected by the pituitary gland. In response to the GnRH hormone, the pituitary gland generates a luteinizing hormone (LH) that is detected by the testes. In response to the LH hormone, the testes produce testosterone.

The production of growth hormone (GH) and insulin-like growth factor 1 (IGF-1) are apparently regulated by similar systems and pathways. The hypothalamus generates a growth hormone releasing hormone (GHRH) that triggers the release of growth hormone (GH) by the pituitary. GHRH is released in pulsatile fashion and the subsequent release of GH from the pituitary is also pulsatile in nature. GH stimulates the liver to increase production and release of IGF-1. Increased levels of IGF-1 promote production of somatostatin, also known as growth hormone inhibiting hormone (GH1H), in the hypothalamus. Somatostatin acts on the hypothalamus and pituitary to decrease production of GHRH and GH. This regulatory system of GHRH, GH, IGF-1, and somatostatin is referred to as the GH/IGF-1 axis.

4. Animal Studies With D-Aspartic Acid

As previously mentioned, levels of testosterone, growth hormone, and insulin-like growth factor 1 in the blood can be increased by simply administering the hormones themselves. The levels can also be increased by adding other hormones (such as gonadotropin releasing hormone or luteinizing hormone) or prohormones that trigger the body to produce the three hormones. The addition of hormones carries the potential for serious side effects and many hormones are available only with a physician's prescription.

Some recent research has indicated that certain non-hormonal compounds may also have an effect on the production of hormones in male mammals. Many experiments have been performed involving the administration of D-aspartic acid or N-methyl-D-aspartate to animals of species ranging from rats to sheep to lower primates. The administration of these two compounds has been performed by injection into the bloodstream. N-methyl-D-aspartate has also been administered orally.

For example, the administration of D-aspartic acid and N-methyl-D-aspartate has been shown to cause an increase in testosterone and growth hormone levels in the animals. Antimo D'Aniello, "D-Aspartic Acid: An Endogenous Amino Acid With An Important Neuroendocrine Role," *Brain Research Reviews*, Vol. 53, No. 2, pp. 215-234 (2007); and R. Boni et al., "Puberty In Monkeys Is Triggered By Chemical Stimulation Of The Hypothalamus," *Proceedings of the National Academy of Sciences*, Vol. 86, No. 7, pp. 2506-2510 (1989). The administration of N-methyl-D-aspartate has been shown to cause an increase in growth rate. G. Xi et al., "Growth Associated Hormones Response And Fat Metabolism Change In Finishing Pigs Fed With N-Methyl-D-Aspartate," *Asian-Australian Journal of Animal Science*, Vol. 15, No. 7, pp. 1026-1030 (2002).

As additional examples, the administration of D-aspartic acid has been shown to stimulate the release of luteinizing hormone from the pituitary, both in-vitro and in-vivo. T. Fukushima et al., "Studies On The Fate of D-Aspartic Acid In Pineal And Pituitary Glands Of Rats And Intravenous Administration," *Proc. Japan. Acad*, Vol. 74, No. B, pp. 18-23 (1998). The administration of D-aspartic acid has been shown to stimulate the release of testosterone from the testes, both in-vitro and in-vivo. Antimo D'Aniello, "Involvement Of D-Aspartic Acid In The Synthesis Of Testosterone In Rat Testes," *Life Sciences*, Vol. 59, No. 2, pp. 97-104 (1996). The administration of D-aspartic acid or N-methyl-D-aspartate has been shown to stimulate growth hormone production from the pituitary gland both in-vitro and in-vivo. Antimo D'Aniello et al., "Occurrence Of D-Aspartic Acid and N-Methyl-D-Aspartic Acid In Rat Neuroendocrine Tissues And Their Role In The Modulation Of Luteinizing Hormone And Growth Hormone Release," *The FASEB Journal*, Vol. 14, pp. 699-714 (2000).

5. Human Studies With D-Aspartic Acid

No studies have examined the effects of D-aspartic acid or N-methyl-D-aspartate on male humans. It is well known that different species of mammals often have different responses to hormones. Therefore, it is unknown whether, and to what degree, the administration of D-aspartic acid compounds in different ways and at different levels to male humans causes an increase in levels of testosterone, growth hormone, and insulin-like growth factor 1.

Accordingly, there is a demand for a method of improving the physical condition of adult male humans of all ages by increasing their levels of testosterone, growth hormone, and insulin-like growth factor 1 without the administration of hormones or prohormones.

SUMMARY OF THE INVENTION

One general object of this invention is to provide an improved method of enhancing the physical condition of adult male humans of all ages by increasing their levels of testosterone, growth hormone, and/or insulin-like growth factor 1 without the administration of hormones.

I have invented a method of improving the physical condition of an adult male human. The method comprises administering an effective amount of a D-aspartic acid compound to an adult male human.

The method of this invention improves the physical condition of adult male humans of all ages by increasing their levels of testosterone, growth hormone, and/or insulin-like growth factor 1 without the administration of hormones. The method comprises the administration of D-aspartic acid and/or its biological equivalent derivate compounds. D-aspartic acid is a chemical that is present in the human body and is generally recognized as safe.

DETAILED DESCRIPTION OF THE INVENTION

1. The Invention In General

The method of the invention comprises the administration of an effective amount of a D-aspartic acid compound to adult human males. It has been surprisingly found that the administration causes an increase in the levels of testosterone, growth hormone, and insulin-like growth factor 1. Increases in these hormones cause, in turn, an improvement in the physical condition of the males.

2. The D-Aspartic Acid Compound

Suitable D-aspartic acid compounds include D-aspartic acid, D-aspartate salts, D-aspartate esters, and other functionally equivalent derivatives such as N-methyl-D-aspartic acid. The D-aspartic acid compound is suitable in its enantiomeric form or as the racemic mixture. The preferred compound is DL-aspartic acid because of its ready availability and low cost.

3. Administration

The D-aspartic acid compound is administered in any known way that results in the compound entering the bloodstream. For example, the compound is orally ingested, injected directly into the bloodstream, administered via patches, and the like. The preferred method of administration is by oral ingestion. D-aspartic acid is well tolerated and is effectively taken into the bloodstream through the digestive tract.

The D-aspartic acid compound is conveniently ingested as a powder or is dissolved in a suitable liquid. For example, D-aspartic acid has substantial solubility in water and is well suited for addition to conventional aqueous beverages. The D-aspartic acid may have synergistic results with other common nutritional supplements, such as androst-4-ene-3,6,17-trione, marketed as 6-OXO supplement by Proviant Technologies, Inc. of Champaign, Ill.

4. Effective Amount

The D-aspartic acid compound is administered in an amount that is effective to increase the levels of testosterone, growth hormone, and/or insulin-like growth factor 1 in the recipient. In general, the D-aspartic acid compound is administered in an amount of about 1 to 100 grams per day, preferably about 1 to 20 grams per day, and most preferably about 5 to 10 grams per day, computed on the basis of equivalent molar amount of D-aspartic acid. In other words, if the DL-aspartic acid racemic modification is used, the amounts are doubled. If a derivative is used having a molecular weight ten percent greater than that of D-aspartic acid, the amounts are increased by ten percent to provide the same equivalent molar amount.

5. Benefits

The administration of an effective amount of a D-aspartic acid compound has many beneficial effects on adult male humans. The administration causes an increase in the levels of testosterone, growth hormone, and/or insulin-like growth factor 1 in the recipient, regardless of age. The increases in these hormones, in turn, are believed to cause a large number of improvements in physical condition, including an increase in muscle mass, an increase in strength, a decrease in fat, and a reduction in various aging characteristics. Increases in these hormones are also believed to cause an improvement in sexual performance.

6. Example

The following example is illustrative only.

Example 1

This example illustrates the effects of administering D-aspartic acid to adult male humans.

A group of nine adult males ranging in age from twenty to sixty is divided into three groups of three men each. The division is made so that each group contains a similar age distribution. Blood samples are taken and the levels of testosterone, growth hormone, and insulin-like growth factor 1 are measured.

The men in the first group orally ingest 10 grams of DL-aspartic acid (which includes 5 grams of D-aspartic acid) daily for twenty-one days. The amount is divided into two equal doses, one of which is taken in the morning and one of which is taken in the evening. The men in the second and third groups follow a similar procedure except the men in the second group orally ingest 20 grams of DL-aspartic acid (which includes 10 grams of D-aspartic acid) per day and the men in the third group orally ingest 40 grams of DL-aspartic acid (which includes 20 grams of D-aspartic acid) per day. Blood samples are then retaken. The results show significant increases in the levels of the three hormones in the three groups.

I claim:

1. A method of increasing the levels of testosterone, growth hormone, and/or insulin-like growth factor 1 in an adult male human, the method comprising administering by oral ingestion a D-aspartic acid compound selected from the group consisting of D-aspartic acid, D-Aspartate salts, and D-aspartate esters to an adult male human, wherein said D-aspartic acid compound is administered in an amount and for a time sufficient to increase the levels of testosterone, growth hormone, and/or insulin-like growth factor 1.

2. The method of claim 1 wherein the D-aspartic acid compound is administered in an amount of about 1 to 20 grams of D-aspartic acid equivalent.

* * * * *